United States Patent
Chen

(10) Patent No.: US 8,573,028 B2
(45) Date of Patent: Nov. 5, 2013

(54) ANTISKID PERFORMANCE TESTING APPARATUS FOR SHOE SOLE

(75) Inventor: Zhirong Chen, Zhejiang (CN)

(73) Assignee: Zhejiang Red Dragonfly Footwear Co., Ltd., Zhejiang (CN)

( * ) Notice: Subject to any disclaimer, the term of this patent is extended or adjusted under 35 U.S.C. 154(b) by 345 days.

(21) Appl. No.: 12/999,572

(22) PCT Filed: Jun. 16, 2009

(86) PCT No.: PCT/CN2009/072281
§ 371 (c)(1), (2), (4) Date: Feb. 22, 2011

(87) PCT Pub. No.: WO2009/152756
PCT Pub. Date: Dec. 23, 2009

(65) Prior Publication Data
US 2011/0132068 A1    Jun. 9, 2011

(30) Foreign Application Priority Data
Jun. 20, 2008 (CN) .......................... 2008 1 0062532

(51) Int. Cl.
*G01N 19/02* (2006.01)
(52) U.S. Cl.
USPC ............................................. 73/7
(58) Field of Classification Search
USPC ............................................. 73/7
See application file for complete search history.

(56) References Cited

U.S. PATENT DOCUMENTS 5,576,478 A * 11/1996 Brungraber .................. 73/9

FOREIGN PATENT DOCUMENTS

| CN | 2410635 Y | 12/2000 |
| CN | 101308083 A | 11/2008 |
| CN | 201229250 Y | 4/2009 |
| EP | 0 264 526 A2 | 4/1988 |

OTHER PUBLICATIONS

International Search Report dated Aug. 13, 2009 (with English Translation), 4 pages.

* cited by examiner

*Primary Examiner* — Hezron E Williams
*Assistant Examiner* — Paul West
(74) *Attorney, Agent, or Firm* — Harrity & Harrity, LLP

(57) ABSTRACT

An antiskid performance testing apparatus for shoe sole comprises a base (17), a locating device and a force application device. The force application device includes a power source, a transport mechanism and a force application rod (6). The force application rod (6) is connected with a fixing shaft (8) via a sector turntable (2). The sector turntable (2) is equipped with a circular arc groove, and is sleeved on the fixing shaft (8) via a sleeve (12). A lower end of the force application rod (6) is fixed on the sector turntable (2) via a location pin (3), an upper end of the force application rod (6) is connected with the transport mechanism, and middle of the force application rod (6) is fixed with a slide pin (4). Two ends of the slide pin (4) are located in the circular arc groove of the sector turntable (2). The testing apparatus can test the antiskid performance of shoe under different force angles.

2 Claims, 1 Drawing Sheet

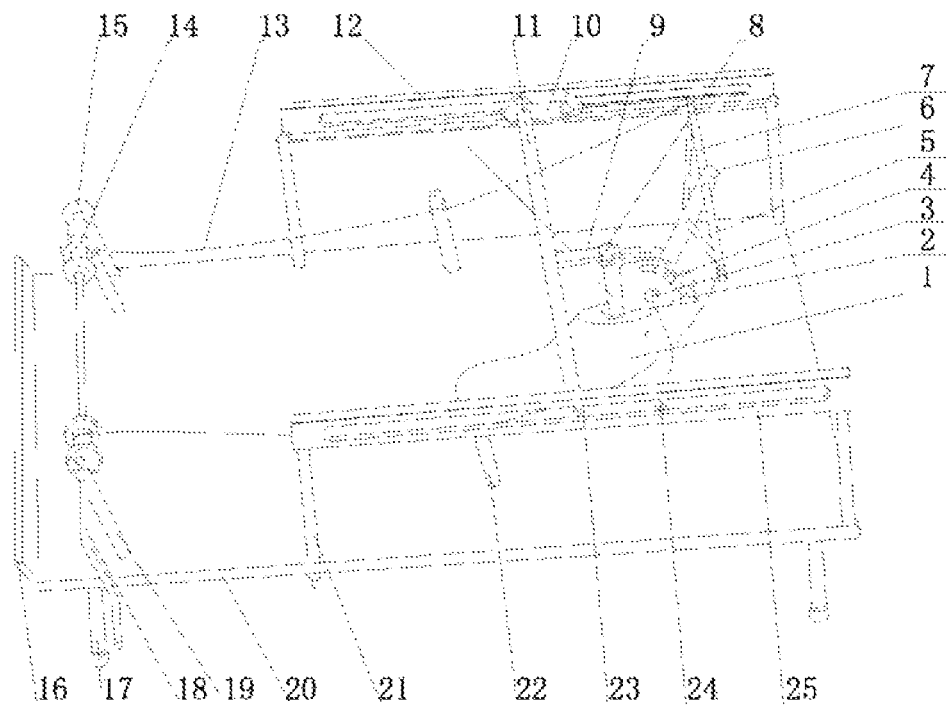

ANTISKID PERFORMANCE TESTING APPARATUS FOR SHOE SOLE

TECHNICAL FIELD

The present invention relates to a performance testing apparatus for shoe, in particular, to an antiskid performance testing apparatus for shoe sole. The present invention is suitable for the testing instrument of antiskid performance for shoe sole used by the shoe research and design organization.

BACKGROUND OF THE INVENTION

The antiskid performance of shoe sole is related to the safety of using the product, and is a main parameter to be considered in designing. The antiskid performance of a type of shoe is usually measured by a skid measuring device. Currently, the antiskid performance of shoe is usually measured by the method as follow: the shoe is located on a specific slide board, then a force is applied on the shoe until it slides, the antiskid performance of the shoe is estimated according to the force. The existing antiskid performance testing apparatus for shoe sole is composed of a base, a locating device and a force application device, the slide board is provided on the base, the locating device is composed of a slideway fixed on the base, a slide bar mounted in the slideway, a fixing shaft connected with the slide bar and a shoe last connected with the fixing shaft, and the force application device comprises a power source and a transport mechanism. The force exerted by the power source is applied to the fixing shaft via the transport mechanism, and makes the shoe sole bear the force by means of the shoe last until it slides. The main shortcoming is the direction of the force acting on the shoe last is fixed and thus the antiskid performance of the shoe can only be simulated and tested in a single state under force, while when people move, the shoe will fall to the ground at different angles, and the existing products cannot test the antiskid performance of the shoe under various angles in a moving state.

SUMMARY OF THE INVENTION

The objective of the present invention is, regarding the shortcoming in the prior art, to provide an antiskid performance testing apparatus for shoe sole that can change the force application direction, and can simulate and test the antiskid performance of the shoe under various force angles in a moving state.

The technical solution for accomplishing the objective of the present invention comprises a base, a locating device and a force application device. The base is provided with a slide board; the locating device comprises a horizontal slideway, a slide bar, a fixing shaft and a shoe last connected with the fixing shaft, two ends of the slide bar are movably mounted in the horizontal slideway, middle of the slide bar is connected with the fixing shaft; the force application device comprises a power source, a transport mechanism and a force application rod; principally, the force application rod is connected with the fixing shaft via a sector turntable, the sector turntable is equipped with a circular arc groove, and is sleeved on the fixing shaft via a sleeve, the lower end of the force application rod is fixed on the sector turntable via a location pin, the upper end of the force application rod is connected with the transport mechanism, and middle of the force application rod is fixed with a slide pin, two ends of the slide pin are located in the circular arc groove of the sector turntable.

In the above technical solution, the upper end of the force application rod is provided with an assistant force application rod, middle of the assistant force application rod is fixed onto the force application rod and is perpendicular to the force application rod.

In the above technical solution, the transport mechanism comprises a transmission shaft, transmission steel wire, two steelwire coils and two guide tubes. The steelwire coils are fixed on the transmission shaft, and the transmission steel wire runs through the guide tube to be fixedly connected with the two ends of the assistant force application rod.

Compared with the prior art, the advantage of the present invention is that the force application rod is connected with the fixing shaft via a sector turntable that is rotatable by 180° pivoting about the fixing shaft, the force application rod can have its position adjusted in the range of 0-90° of the sector turntable, and can simulate different angles when the foot of the human body falls to the ground, so as to test the antiskid performance of the shoe under different force angles.

DESCRIPTION OF THE DRAWING

FIG. 1 is a structural schematic drawing of the present invention.

DETAILED DESCRIPTION

As shown in FIG. 1, the structure of the antiskid performance testing apparatus for shoe sole comprises a base 17, a locating device and a force application device. A slide board 20 is provided on the base 17, this slide board 20 simulates the roughness of ordinary ground, and the end portion of the slide board 20 is provided with a baffle 16. The locating device comprises a horizontal slideway 25, a slide bar 11, a fixing shaft 8 and a shoe last 1 connected there. Two ends of the slide bar 11 are movably mounted in the horizontal slideway 25 via rollers 23 and fix a balance bar 10, the other end of the balance bar 10 is connected with a balance wheel 24, and the balance wheel 24 is located in the horizontal slideway 25 to improve the stability of the movement of the slide bar 11 in the horizontal slideway 25. The middle of the slide bar 11 is connected with the fixing shaft 8 via a connecting bar 9. The lower end of the fixing shaft 8 is inserted into the shoe last 1, the shoe last 1 simulates the human foot, and the horizontal slideway 25 is mounted on the slide board 20 via mounting feet 21. The force application device comprises a power source, a transport mechanism and a force application rod 6 which simulates the crus of the human body in testing. The force application rod 6 is connected with the fixing shaft 8 via a sector turntable 2 which is equipped with a circular arc groove, and is sleeved on the fixing shaft 8 via a sleeve 12 that is rotatable around the fixing shaft 8. The lower end of the force application rod 6 is fixed on the sector turntable 2 via a location pin 3, the upper end of the force application rod 6 is connected with the transport mechanism, and the middle of the force application rod 6 is fixed with a slide pin 4. Two ends of the slide pin 4 are located in the circular arc groove of the sector turntable 2. The radian of the circular arc groove of the sector turntable 2 centering on the location pin 3 is 90°, and the slide pin 4 can be locked at any position within the circular arc groove of the sector turntable 2, to freely adjust the position of the force application rod 6 in the range of 0-90° of the circular arc groove of the sector turntable 2. The sector turntable 2 is rotatable by 180° with respect to the fixing shaft 8, and is fixed by a nut at any position in the range of 0-180°. The upper end of the force application rod 6 is provided with an assistant force application rod 7, the middle of which is fixed onto the force application rod 6 and is perpendicular to the force application rod 6. Support bars 5 are provided between the two ends of the assistant force application rod 7 and the middle portion of the force application rod 6. The transport mechanism comprises a transmission shaft 18, transmission steel wire 13, two steelwire coils 14 and two guide tubes 22. The steelwire coils 14 are fixed on the transmission shaft 18, and the transmission steel wire 13 passes through the guide tube 22 to be fixedly connected with the two ends of the assistant force application rod 7. The transmission shaft 18 is mounted on the slide board 20 via a fixing tube 19. An end portion of the transmission shaft 18 is provided with a transmission connector 15 that is connected with a moment output shaft of the power source. The distances between the left and right steelwire coils 14, and between the left and right guide tubes 22 are the same as that between the two points connecting the steel wire 13 at each of the two ends of the assistant force application rod 7. An ergometer is equipped between the slide bar 11 and the horizontal slideway 25, and also can be connected onto the transmission shaft 18. Force sensor and spring ergometer can be used for testing the force, which is known technologies, and will not be described in detail herein.

In the above embodiment, the sector turntable 2 can also be fixedly connected with the fixing shaft 8. Thus, the fixing shaft 8 is rotatably connected with the connecting bar 9 and the shoe last 1, and the fixing shaft 8 is fixedly connected with the connecting bar 9 via a nut when the testing position is selected. That is, when the nut is unscrewed, the fixing shaft 8 is rotatable with respect to the connecting bar 9 and the shoe last 1, and when the nut is fastened, the fixing shaft 8 is fixedly connected with the connecting bar 9, and the test is started.

What is claimed is:

1. An antiskid performance testing apparatus for shoe sole, the antiskid performance testing apparatus comprising:
   a base (17), a locating device and a force application device, a slide board (20) being provided on the base (17),
      the locating device comprising a horizontal slideway (25), a slide bar (11), a fixing shaft (8) and a shoe last (1) connected with the fixing shaft (8),
      two ends of the slide bar (11) being movably mounted in the horizontal slideway (25),
      a middle of the slide bar (11) being connected with the fixing shaft (8),
   the force application device comprising a power source, a transport mechanism and a force application rod (6),
      wherein the force application rod (6) is connected with the fixing shaft (8) via a sector turntable (2), the sector turntable (2) is equipped with a circular arc groove and is sleeved on the fixing shaft (8) via a sleeve (12), a lower end of the force application rod (6) is fixed on the sector turntable (2) via a location pin (3), an upper end of the force application rod (6) is connected with the transport mechanism, and a middle of the force application rod (6) is fixed with a slide pin (4),
      two ends of the slide pin (4) are located in the circular arc groove of the sector turntable (2),
      wherein the upper end of the force application rod (6) is provided with an assistant force application rod (7), a middle of the assistant force application rod (7) is fixed on the force application rod (6) and is perpendicularlication rod (6), and
   wherein the transport mechanism comprises a transmission shaft (18), a transmission steel wire (13), two steelwire coils (14) and two guide tubes (22),
      the steelwire coils (14) are fixed on the transmission shaft (18),
      the transmission steel wire (13) passes through the guide tube (22) to be fixedly connected with two ends of the assistant force application rod (7).

2. The antiskid performance testing apparatus for shoe sole according to claim 1, wherein a number of the horizontal slideway (25) is two, each of the horizontal slideways (25) is provided with a slot, one end of the slide bar (11) is movably provided in one of the horizontal slideways (25), and another end of the slide bar (11) is movably provided in another one of the horizontal slideways (25).

\* \* \* \* \*

UNITED STATES PATENT AND TRADEMARK OFFICE
CERTIFICATE OF CORRECTION

PATENT NO. : 8,573,028 B2  
APPLICATION NO. : 12/999572  
DATED : November 5, 2013  
INVENTOR(S) : Zhirong Chen Page 1 of 1

It is certified that error appears in the above-identified patent and that said Letters Patent is hereby corrected as shown below:

In the Claims

Please correct Claim 1 (Column 4, Line 24) to read as follows:

(6) and is perpendicular to the force application rod (6), and

Signed and Sealed this  
Eighteenth Day of February, 2014

Michelle K. Lee  
*Deputy Director of the United States Patent and Trademark Office*